United States Patent
Wu et al.

(10) Patent No.: US 7,740,858 B2
(45) Date of Patent: Jun. 22, 2010

(54) SARS-COV-SPECIFIC B-CELL EPITOPE AND APPLICATIONS THEREOF

(75) Inventors: Han-Chung Wu, Taipei (TW); I-Ju Liu, Taipei (TW); Chien-Yu Chiu, Taipei (TW)

(73) Assignee: National Taiwan University (TW)

( * ) Notice: Subject to any disclaimer, the term of this patent is extended or adjusted under 35 U.S.C. 154(b) by 536 days.

(21) Appl. No.: 10/945,648

(22) Filed: Sep. 21, 2004

(65) Prior Publication Data

US 2006/0062804 A1   Mar. 23, 2006

(51) Int. Cl.
*A61K 39/38* (2006.01)
*A61K 39/12* (2006.01)
*A61K 39/00* (2006.01)
*A61K 39/215* (2006.01)

(52) U.S. Cl. .............. 424/186.1; 424/184.1; 424/185.1; 424/204.1; 424/221.1; 530/300

(58) Field of Classification Search ........................ None
See application file for complete search history.

(56) References Cited

U.S. PATENT DOCUMENTS

2005/0100883 A1 * 5/2005 Wang et al. .................... 435/5
2005/0106563 A1 * 5/2005 Huang et al. ................... 435/5

FOREIGN PATENT DOCUMENTS

CN    1475571 A  *  2/2004

OTHER PUBLICATIONS

Miura et al. Interaction of Ash/Grb-2 via its SH3 domains with neuron-specific p150 and p65. Biochemical Journal 1996, vol. 316, pp. 639-645.*
Wang et al. Assessment of Immunoreactive Synthetic Peptides from the Structural Proteins of Severe Acute Respiratory Syndrome Coronavirus. Clinical Chemistry 2003, vol. 49, No. 12, p. 1989-1996.*
Rota et al. Characterization of a Novel Coronavirus Associated with Severe Acute Respiratory Syndrome. Science 2003, vol. 300, No. 5624, p. 1394-1399.*
I-Ju Liu et al., Disease-Specific B Cell Epitopes for Serum Antibodies from Patients with Severe Acute Respiratory Syndrome (SARS) and Serologic Detection of SARS Antibodies by Epitope-Based Peptide Antigens, *The Journal of Infectious Diseases* 2004; 190:797-809.

* cited by examiner

*Primary Examiner*—Jeffrey S Parkin
*Assistant Examiner*—Louise Humphrey
(74) *Attorney, Agent, or Firm*—Ostrolenk Faber LLP

(57) ABSTRACT

Disclosed is SARS-CoV-specific B-cell epitope and applications thereof. The epitopes are peptides and can either be expressed in phages or synthesized to diagnose SARS patients accurately. High sensitivity and specificity of the serologic detection are achievable by using a plurality of SARS-CoV-specific B-cell epitope-based peptides. Therefore, the peptides can be applied to SARS diagnosis and have potentials to be immunogens for producing antibodies against SARS.

7 Claims, 1 Drawing Sheet

SEQUENCE LISTING

<160> NUMBER OF SEQ ID NOS: 15

<210> SEQ ID NO 1
<211> LENGTH: 3
<212> TYPE: PRT

-continued

<213> ORGANISM: SARS virus

<400> SEQUENCE: 1

Pro Pro Asn
1

<210> SEQ ID NO 2
<211> LENGTH: 10
<212> TYPE: PRT
<213> ORGANISM: SARS virus

<400> SEQUENCE: 2

Gln Glu Glu Pro Pro Asn Thr Glu Asp Ser
1               5                   10

<210> SEQ ID NO 3
<211> LENGTH: 3
<212> TYPE: PRT
<213> ORGANISM: SARS virus

<400> SEQUENCE: 3

Val Lys Ile
1

<210> SEQ ID NO 4
<211> LENGTH: 13
<212> TYPE: PRT
<213> ORGANISM: SARS virus

<400> SEQUENCE: 4

Pro Val Lys Ile Asp Asn Ala Ser Pro Ala Ser Thr Val
1               5                   10

<210> SEQ ID NO 5
<211> LENGTH: 3
<212> TYPE: PRT
<213> ORGANISM: SARS virus

<400> SEQUENCE: 5

Thr Asn Val
1

<210> SEQ ID NO 6
<211> LENGTH: 4
<212> TYPE: PRT
<213> ORGANISM: SARS virus

<400> SEQUENCE: 6

Asn Pro Phe Glu
1

<210> SEQ ID NO 7
<211> LENGTH: 3
<212> TYPE: PRT
<213> ORGANISM: SARS virus

<400> SEQUENCE: 7

Pro Leu Pro
1

<210> SEQ ID NO 8
<211> LENGTH: 4
<212> TYPE: PRT
<213> ORGANISM: SARS virus

```
<400> SEQUENCE: 8

Val Ile Thr Pro
1

<210> SEQ ID NO 9
<211> LENGTH: 10
<212> TYPE: PRT
<213> ORGANISM: SARS virus

<400> SEQUENCE: 9

Ser Val Ile Thr Pro Gly Thr Asn Ala Ser
1               5                   10

<210> SEQ ID NO 10
<211> LENGTH: 4
<212> TYPE: PRT
<213> ORGANISM: SARS virus

<400> SEQUENCE: 10

Pro Leu Lys Pro
1

<210> SEQ ID NO 11
<211> LENGTH: 10
<212> TYPE: PRT
<213> ORGANISM: SARS virus

<400> SEQUENCE: 11

Asp Pro Leu Lys Pro Thr Lys Arg Ser Phe
1               5                   10

<210> SEQ ID NO 12
<211> LENGTH: 10
<212> TYPE: PRT
<213> ORGANISM: SARS virus

<400> SEQUENCE: 12

Val Lys Ile Asp Asn Ala Ser Pro Ala Ser
1               5                   10

<210> SEQ ID NO 13
<211> LENGTH: 12
<212> TYPE: PRT
<213> ORGANISM: SARS virus

<400> SEQUENCE: 13

Val Lys Ile Pro Gln His Met His Pro Leu Pro Ile
1               5                   10

<210> SEQ ID NO 14
<211> LENGTH: 12
<212> TYPE: PRT
<213> ORGANISM: SARS virus

<400> SEQUENCE: 14

Lys Pro Pro Asn Pro Arg Pro Thr Met Ser Leu Trp
1               5                   10

<210> SEQ ID NO 15
<211> LENGTH: 12
```

```
-continued
<212> TYPE: PRT
<213> ORGANISM: SARS virus

<400> SEQUENCE: 15

Val Ile Thr Pro Gln Pro Phe Lys Asn Thr His Arg
1               5                   10
```

SARS-COV-SPECIFIC B-CELL EPITOPE AND APPLICATIONS THEREOF

The present invention incorporates by reference the Sequence Listing presented in the .txt file identified as "10945648 0809 Sub Seq Listing.txt" created Aug. 6, 2009 (size: 4000 bytes).

BACKGROUND OF THE INVENTION

1. Field of the Invention

The present invention relates to SARS-CoV-specific B-cell epitopes and the epitope-based peptides, which can be applied to SARS diagnosis and have potentials to be the immunogens for producing antibodies against the SARS virus or for development of a SARS vaccine.

2. The Prior Arts

In Feb. 26, 2003, an American businessman was admitted to a hospital in Hanoi after falling ill while on a business trip to Vietnam. He died after transferring to Hong Kong for treatment. Since then, cases of atypical pneumonia combined with respiratory tract infections are reported in Hong Kong, Vietnam, Singapore, and Canada, respectively. The symptoms of this atypical pneumonia including diffuse pneumonia and respiratory failures are more serious than those of pneumonia caused by virus or bacteria. It was, therefore, named Severe Acute Respiratory Syndrome (SARS). WHO formally announced that the disease agent of SARS was identified as a SARS-associated coronavirus (SARS-CoV) on Apr. 16, 2003. This new strain of Corona virus is designated as SARS-CoV that has not been previously identified in humans or animals and cannot be excluded from mutant virus. What is known about SARS-CoV so far is that human beings have no antibody protection against the virus. The virus has a very strong infection rate, propagation ability, toxicity and pathogenicity which may cause lung fibrosis to the patient, even induce shortness of breath or life-threatening respiratory failure and result in death.

According to the case definitions by WHO (World Health Organization), which are revised on May 1, 2003, are shown in the following:

Suspect Case:
1. A person presenting after 1 Nov. 2002 with history of:
   high fever (>38° C.)
   AND
   cough or breathing difficulty
   AND one or more of the following exposures during the 10 days prior to onset of symptoms:
   close contact with a person who is a suspect or probable case of SARS;
   history of travel, to an area with recent local transmission of SARS
   residing in an area with recent local transmission of SARS
2. A person with an unexplained acute respiratory illness resulting in death after 1 Nov. 2002, but on whom no autopsy has been performed
   AND one or more of the following exposures during to 10 days prior to onset of symptoms:
   close contact, with a person who is a suspect or probable case of SARS;
   history of travel to an area with recent local transmission of SARS
   residing in an area with recent local transmission of SARS Probable Case:
1. A suspect case with radiographic evidence of infiltrates consistent with pneumonia or respiratory distress syndrome (RDS) on chest X-ray (CXR).
2. A suspect case of SARS that is positive for SARS coronavirus by one or more assays.
3. A suspect case with autopsy findings consistent with the pathology of RDS without an identifiable cause.

The main symptoms of SARS include high fever (above 38° C.), dry cough, and shortness of breath or breathing difficulties. Changes in chest X-rays indicative of pneumonia also occur. SARS may be associated with other symptoms, including headache, muscular stiffness, and loss of appetite, malaise, confusion, rash and diarrhea. In most serious cases, the respiratory illness progresses to diffuse pneumonia, poor oxygen exchange, which causes lack of oxygen in lung and severe respiratory difficulty. The disease can progressively worsen and eventually result in death. The incubation period ranges from 2 to 7 days generally, and may get more than 10 days with the longest period and 3 to 5 days with the common period. It could extend to 14 days to allow an extra margin of safety.

Due to the long incubation period and the highly contagious characteristics of SARS-CoV, accurate and quick laboratory diagnostics are still not available and SARS diagnosis remains dependent on clinical findings. Therefore, many people are developing the technology for rapid detection of SARS. SARS diagnostic methods are mainly based on Polymerase Chain Reaction (PCR) technology up to now. When SARS-CoV RNA is detected by RT-PCR, at least two different clinical specimens (such as nasal swabs and stools), clinical specimens from the same portion but acquired at different dates (such as nasal swabs taken twice or more times), or an original specimen subjected to two respective different assays or repeated PCR. Although detection of SARS-CoV can be accomplished through PCR, this technology has several limitations. It may take several days to confirm the SARS-CoV from patient samples. The labor requirements and capital resources are large and the cost is not low enough for large-scale screening.

In early stage of the disease, the SARS patients are offered with supportive treatments to prevent the deterioration of the disease. Active treatments are offered for those developed early symptoms after close contact with SARS patients (short incubation period), the weak elderly, the small child, or patients accompanied with other diseases.

Treatments of SARS include antiviral medications (such as oseltamivir or ribavirin) and antibiotics (to prevent bacterial infection as well) since onset of SARS symptoms within 5 days (the early stage). However, no medication has been proven to cure SARS so far. A rapid diagnostic test that can reliably diagnose SARS-CoV infection during the early phase of illness, which is easy to manipulate, labor-saving and cost-effective, as well as an effective treatment drugs, are the key issues needed to prevent the spread of SARS.

SUMMARY OF THE INVENTION

A primary object of the present invention is to provide SARS-CoV-specific B-cell epitope through serological screening, which can be used for the development of a rapid, simple, low cost test for commercially available, large scale screening of SARS patients, for the vaccine and therapeutic antibody developments.

Another object of the present invention is to provide a method for selection of disease-specific epitopes by phage display and diagnosing SARS patients using the epitope-based peptides specific for SARS-CoV.

To accomplish the abovementioned objects, the present invention identifies SARS virus specific B-cell epitopes for investigation of the pathogenesis of SARS. These B-cell epitopes are applied to develop SARS diagnostic reagents, vaccines and therapeutic antibodies.

Phage display biopanning technology is employed to screen the SARS CoV-specific B-cell epitopes. Library of phage displayed random peptides are panned with sera from SARS patients to identify the phages that can bind specifically with epitopes.

The theory of phage display technology is based on assembly of functional bacteriophage lambda virions incorporating a random sequence. The peptide encoded randomized sequence is expressed with the capsid protein III as a protein fusion. A library consisting of the phages expressing peptide sequence encoded the random sequences is termed phage-displayed random peptide library. Based on the phage display technology, a phage-displayed random peptide library is established for screening of the phages expressing SARS-CoV-specific B-cell epitopes. Next, purified antibodies from normal serum are linked to protein G magnetic microbeads. The phage displayed-peptide library is absorbed onto the above-mentioned beads there after. The phage clones bound to normal serum are removed by this step. The pre-cleared phage library, which does not bind to normal serum, is selected onto the protein G magnetic microbeads bound antibody from the serum of SARS patients. Phage clones containing SARS-CoV epitopes bind to the antibody in SARS serum. The phages with SARS-CoV epitopes are obtained through protein G magnetic microbead adsorption. Three rounds of selection are performed to remove the phage clones with low specificity and to obtain phage clones with high specificity to antibody against SARS-CoV.

The resulting phage clones are isolated and analyzed with enzyme-linked immunosorbent assay (ELISA) with serum from normal human or SARS patients. Those epitope-based peptides in candidate phage clones show highly specific binding activity toward SARS patient serum but not normal serum are sequenced and compared with the novel coronavirus from SARS patients. The peptide sequences expressed in the phages are partial similar to SARS-CoV.

The detection sensitivity and specificity are evaluated by binding the peptides in the phages to serum from SARS patient and normal serum (as the control group) respectively. To reconfirm the binding specificity of these peptides, a synthetic peptide antigen is also used to do the same detection experiment.

Depending on the peptides used, high sensitivity of 95.4% for detecting serum from SARS patients and high specificity of 94.7-100% for detecting normal serum are achievable. Detection with a plurality of peptides is effective to elevate the detection sensitivity and is advantageous for detection accuracy.

Therefore, SARS-CoV-specific epitopes and epitope-based peptides according to the present invention can be applied to SARS diagnosis, and have potentials for development of antibodies against SARS-CoV or SARS vaccine. In addition, the present invention provides an effective and rapid way to screen disease-specific epitopes and to develop a method for disease diagnosis.

The present invention is further explained in the following embodiment illustration and examples. It is realized that these are not to be construed as limiting the scope of the invention but as merely providing illustrations of some of the presently preferred embodiments of this invention. The person skilled in the art may make various modifications and changes without departing from the scope and spirit of the present invention.

DETAILED DESCRIPTION OF THE PREFERRED EMBODIMENT

Figure 1:
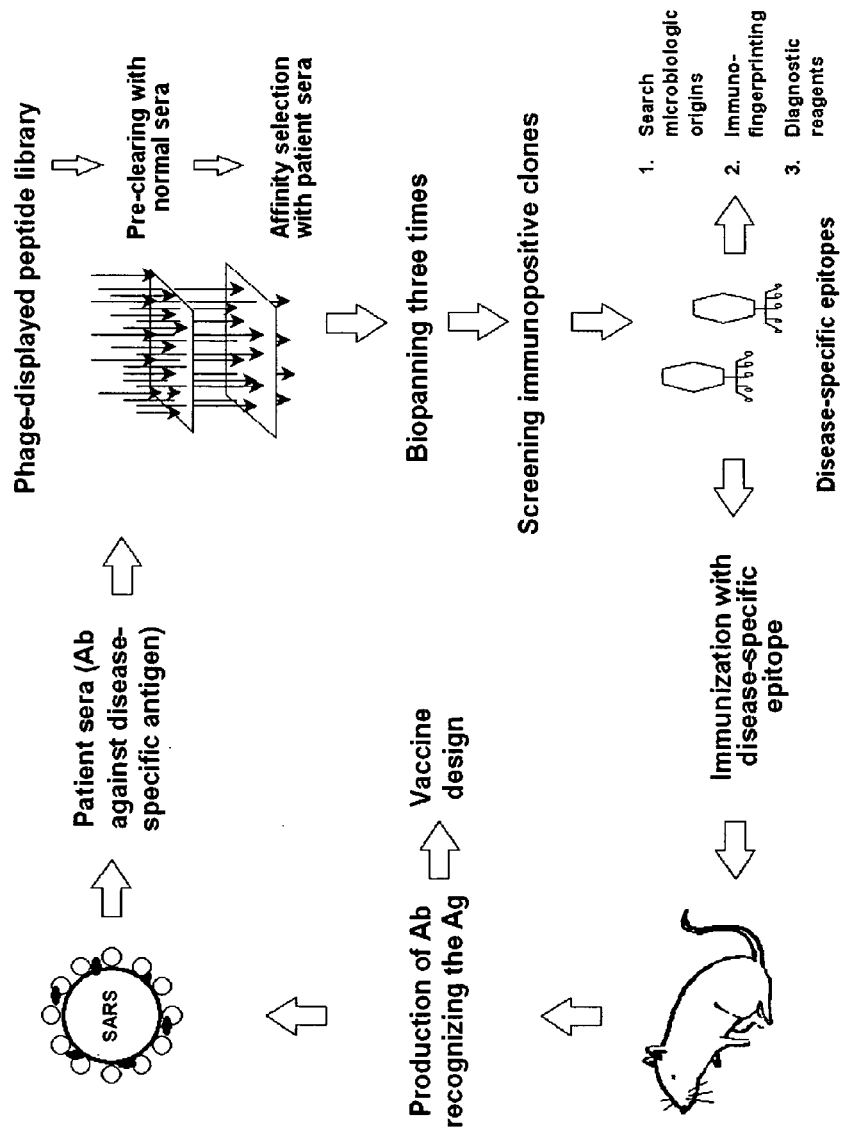
FIG. 1 shows the principle of selection of SARS-CoV-specific epitopes employed in this study through screening on a phage-displayed random peptide library.

FIG. 1 shows the principle of phage display technology in screening SARS-CoV-specific epitopes in the present invention. According to the procedures, SARS disease-specific epitopes can be screened out by preparing a phage display peptide library, pre-cleaning with normal sera, affinity selection with patient sera, biopanning three times, and further screening immuno-positive clones with ELISA. Also, these phage-displayed peptide sequences are aligned to analyze epitopes and binding motif of SARS antibodies. The SARS-specific epitopes can apply to immunize animals, such as mice or rabbits, to produce antibodies recognizing and against SARS-CoV. Also, the screened SARS-CoV-specific epitope-based peptides can be used to diagnose the SARS patients correctly and quickly with general immunoassays like ELISA or other assays.

First, a phage-displayed peptide library is established by fusing sequences from the library of New England BioLabs (New England BioLabs, Inc., Beverly, Ma., USA) to gene III of phages. The phage clones in the library is screened through the biopanning protocol for several rounds to obtain the clones binding to antibodies from SARS patient sera.

Furthermore, the resulting phage clones are analyzed with ELISA with sera from SARS patients. Phage clones show specific binding activity toward antibodies in serum from SARS patients are selected.

Phage clones identified by ELISA are amplified in *E. coli*. The inserted DNA sequences in these phage clones are determined, which contain 36 nucleotide bases and accordingly encode 12 amino acids. These phage-displayed peptide sequences are aligned with MacDNASIS (Hitachi Software Engineering Co., Ltd., Japan) software to analyze epitopes and binding motif of SARS antibodies.

To prove the binding specificity of these selected phage clones, the serial diluted phage clones are incubated with either SARS patient serum or normal serum respectively. ELISA is carried out for analysis after incubation. The immuno-positive phage clones show high binding activity toward SARS patients' serum but not toward normal serum.

At last, the immuno-positive phage clones or the epitope-based synthetic peptides are used to react with serum from SARS patients and healthy donors to evaluate to the diagnostic sensitivity and specificity.

Example 1

Affinity Selection of Phages by Biopanning

Random sequences encoding phage-displayed peptides containing 12 residues from the library of New England BioLabs (New England BioLabs, Inc., Beverly, Ma., USA) are fused to gene III of the phage to prepare a phage-displayed peptide library expressing the randomized sequence. Next, purified IgGs from normal serum are linked to protein G magnetic microbeads. A pre-cleared procedure is performed through binding the phage displayed peptide library (4×10$^{10}$ pfu) onto the beads, and removing those phages absorbed to the beads. The pre-cleared phage library is selected onto magnetic microbeads with the IgGs purified from the serum of SARS patients at 4° C. for one hour. The unbound phage clones are removed and the magnetic beads are washed extensively with solution containing PBS and 0.5% Tween-20. The bound phages are eluted with glycine buffer (pH 2.2), neutralized with Tris buffer (pH 9.1) and amplified in E. coli. After purification of the selected phage clones, the concentration of the phages clones (plaque forming units per ml, pfu/ml) is determine. The phage clones are used for subsequent rounds of selection and two more rounds of selection are performed to remove the phages with low specificity. Biopanning protocol for the second round and the third round are identical to the first round except the added phage doses are 2×10$^{11}$ pfu. The resulting high specific phage clones are spread on LB/IPTG/X-Gal plates and stored at 4° C. for further studies.

Example 2

Screening and Identification of Immuno-Positive Phage Clones with ELISA

The phage clones selected from Example 1 are further screened and identified by the following procedures. ELISA plate is coated with 100 μl of 100 μg/ml of anti-human antibody in 0.1 M NaHCO$_3$ (pH 8.6) at room temperature for two hours and blocked with blocking buffer (1% BSA, bovine serum albumin) at 4° C. overnight.

One hundred fold diluted SARS patient serum is plated onto anti-human antibody-coated plates and incubated at room temperature for one hour. The plates are washed three times with PBST$_{0.1}$ (Phosphate buffer saline containing 0.1% Tween 20). 10$^9$ pfu of the phage clones with high specificity toward SARS patient antibodies are added to the plates and cultivated at room temperature for one hour with agitation and washed six times with PBST$_{0.5}$ (Phosphate buffer saline containing 0.5% Tween 20). Then, the plates are incubated with 1:5000 diluted horseradish peroxidase (HRP)-conjugated anti-bacteriophage M13 antibody (Pharmacia # 27-9411-01) in blocking buffer at room temperature for one hour. The plates are rinsed with PBS buffer six times and subsequently incubated with the peroxidase substrate o-phenylenediamine dihydrochloride (OPD; Sigma, Germany) and hydrogen peroxide. The reaction is stopped with 3N HCl, and absorbance of the plate is read using a microplate ELISA reader at 490 nm.

From serum of three SARS patients, those phage clones with high binding specificity to SARS serum antibodies are designated as Table 1.

Table 1 shows that forty-nine, twenty-four, sixty-five phage clones are selected from seventy-two phage clones, which are immuno-positive to patient serum SP1, SP2 and SP3 respectively. The selected phage clones bind specifically to antibodies in SARS patient serum but not to normal serum.

Example 3

DNA Sequencing and Program Analysis

The phage clones selected from Example 2 are amplified and precipitated with one-sixth volume of polyethylene glycol-NaCl solution (20% (w/v) PEG-8000 and 2.5M NaCl). The precipitated phage pellets are resuspended in 100 μL of iodine buffer (10 mM Tris-HCl, pH 8.0; 1 mM EDTA; 4M NaI) at room temperature for 10 min after adding 250 μL of ethanol.

Phage DNA is isolated from the pellet after centrifugation at 12,000×g for 10 min, washed with 70% ethanol, dried, and resuspended in 50 μl of distilled water.

The DNA sequences of purified phages are determined according to the dideoxynucleotide chain termination method with an automated DNA sequencer (ABI PRISM 377, Perkin-Elmer, Calif., USA). The phage-displayed peptide sequences are translated and aligned using MacDNASIS software (Hitachi Software Engineering Co., Ltd., Japan).

The phage-displayed peptide sequences selected by patient serum SP1, SP2 and SP3 are aligned respectively. Furthermore, the peptide sequences are aligned with complete genome of SARS coronavirus.

Table 2 shows that two binding motifs are highly conserved in many immuno-positive phage clones selected by patient serum SP1 and are exactly corresponded to amino acid residues of the novel SARS-CoV. One motif (SEQ ID NO:1) contains three amino acid residues, showing a consensus motif of proline (Pro, P)-proline (Pro, P)-asparagine (Asn, N), which is exhibited in many immuno-positive phage clones and is only corresponded to amino acid residues 1184-1186 in SEQ ID NO:2 of the SARS coronavirus CDS2. Another binding motif (SEQ ID NO: 3) with the sequence of valine (Val, V)-lysine (Lys, K)-isoleucine (Ile, I), is highly conserved in many immuno-positive phage clones and only corresponds to amino acid residues 18-20 in SEQ ID NO: 4 of the SARS coronavirus CDS4.

From table 3, it shows that three main binding motifs are conserved in immuno-positive phage clones selected by patient serum SP2. One motif (SEQ ID NO:5) contains three amino acid residues, which is threonine (Thr, T)-asparigine (Asn, N)-valine (Val, V). Another binding motif (SEQ ID NO: 6) contains four amino acid residues with the sequence of asparigine (Asn, N)-proline (Pro, P)-phenylalanine (Phe, F)-glutamic acid (Glu, E). And one motif (SEQ ID NO: 7) contains three amino acid residues, which is proline (Pro, P)-leucine (Leu, L)-proline (Pro, P).

Table 4 shows that two binding motifs are highly conserved in many immuno-positive phage clones selected by patient serum SP3 and are exactly corresponded to amino acid residues of the SPIKE glycoprotein of SARS-CoV, CDS3. One motif (SEQ ID NO: 8) contains four amino acid residues, showing a consensus motif of valine (Val, V)-isoleucine (Ile, I)-threonine (Thr, T)-proline (Pro, P), which is exhibited in immuno-positive phage clones and is only corresponded to amino acid residues 583-586 in SEQ ID NO: 9 of the SPIKE of SARS-CoV CDS3. Another binding motif (SEQ ID NO: 10) with the sequence of proline (Pro, P)-leucine (Leu, L)-lysine (Lys, K)-proline (Pro, P), is highly conserved immuno-positive phage clones and is only corresponded to amino acid residues 791-794 in SEQ ID NO: 11 of the SPIKE of SARS-CoV CDS3.

Example 6

Detection of SARS Patient Serum Samples with Immuno-positive Phage Clones and Epitope-Based Antigens Serum samples are from sixty-six SARS positive patients whose illness met the CDC case definition and twenty-two healthy donors. Phage clones SP1-1, SP1-20, SP2-27, SP3-29 are applied in IgG capture ELISA to screen the serum samples obtained in convalescent stage. Also, an epitope-based synthetic peptide SP3M (SEQ ID NO: 12, VKIDNASPAS), which is ten amino acid residues located in the CDS4 of SARS-CoV, is applied to the ELISA assay.

In ELISA assays with phage clones, the ELISA plates are coated with 10 μg/ml purified anti-human IgG capture antibodies (Jackson ImmunoResearch Labs, West Grove, Pa.), blocked with PBSB (1% BSA in PBS) and then incubated with the 1:100 diluted serum samples at room temperature for one hour. Plates are washed three times with $PBST_{0.1}$ and $1 \times 10^9$ pfu of immuno-positive phage particles are added. Incubation is carried out for one hour at room temperature, and plates are washed six times with $PBST_{0.1}$. In the blocking procedure, 1:5000 blocking buffer containing diluted HRP-conjugated anti-bacteriophage M13 antibody is added into the plates, and the other ELISA steps described in Example 2 are followed. The mean optical density at 490 nm ($OD_{490}$ nm) plus 3 times of the standard deviation is used to determine the cut-off value.

In case of ELISA assay with epitope-based synthetic peptide SP3M, the ELISA plates are coated with 10 μg/ml peptide antigen at 50 μl/well, and incubated at 4° C. for six hours. After being washed with $PBST_{0.1}$, the plates are blocked with PBSB at 4° C. overnight, and are incubated with the tested serum samples, diluted 1:100, at room temperature for one hour. HRP-conjugated, goat anti-human IgG (Jackson ImmunoResearch Labs), diluted 1:20,000, is added to the microtiter plates, and the other ELISA steps described in Example 2 are followed. The mean optical density at 490 nm ($OD_{490}$ nm) plus 3 times of the standard deviation is used to determine the cut-off value.

Table 5 illustrates sensitivity and specificity of the serologic tests. Sensitivity of the serologic tests using SP1-1, SP1-20, SP2-27, SP3-29 and SP3M is 57.6% (38/66), 45.5% (30/66), 15.2% (10/66), 36.4% (24/66), 60.6% (40/66), respectively. Sensitivity is highly elevated to 95.4%(63/66) if all the tested phage displayed peptides and SP3M are taken consideration together. Applying a combination of SARS specific epitopes to the tests will bring in a high sensitivity in diagnosing SARS. In contrast, specificity of the serologic tests for serum samples obtained from healthy donors is 95.4-100%. Therefore, the SARS specific epitopes are highly specific for serum samples from healthy donors.

From the illustrations and examples above, the SARS virus-specific B-cell epitopes provided in the present invention are applicable to SARS diagnosis. Usage of a plurality of SARS virus-specific B-cell epitopes is effective to increase the sensitivity and accuracy of the diagnosis assay. Either immuno-positive phage clones or synthetic epitope-based peptides are available for the SARS diagnosis assay.

Moreover, since those screened epitopes are highly specific to antibodies from SARS patient serum, they have great potentials to develop a SARS vaccine. Also, the epitopes can be taken as a portion of an immunogen to produce antibodies against the SARS virus.

TABLE 1

Immuno-positive phage clones selected from SARS patient serum

| Patient | Immuno-positive phage clones | Note |
|---------|------------------------------|------|
| SP1 | SP1-1, 3, 4, 5, 7, 8, 9, 12, 13, 14, 16, 18, 19, 20, 24, 25, 26, 28, 29, 30, 31, 32, 34, 35, 36, 38, 39, 40, 42, 43, 45, 46, 47, 48, 49, 50, 51, 52, 53, 54, 57, 58, 60, 61, 64, 65, 66, 69 and 72 | 49 phage clones selected from 72 phage clones |
| SP2 | SP2-2, 3, 4, 10, 16, 23, 25, 27, 33, 40, 45, 46, 47, 50, 51, 52, 53, 55, 56, 58, 61, 62, 63, 68 | 24 phage clones selected from 72 phage clones |
| SP3 | SP3-1, 3, 4, 5, 6, 7, 8, 9, 10, 11, 12, 14, 16, 17, 19, 20, 21, 23, 24, 25, 26, 27, 28, 29, 30, 31, 32, 33, 34, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71 | 65 phage clones selected from 72 phage clones |

TABLE 2

Alignment of phage-displayed peptide sequences with complete genome of SARS-CoV[a]

| Virus or clone | Peptide sequence |
|---|---|
| Virus | |
| SARS[1] | $^{CDS2\text{-}1181}$ Q E E P[b] P N T E D S $^{1190}$ |
| SARS[2] | $^{CDS2\text{-}1181}$ Q E E P P N T E D S $^{1190}$ |
| SARS[3] | $^{CDS2\text{-}1181}$ Q E E P P N T E D S $^{1190}$ |
| Clone | |
| SP1-20 | K P P N P R P T M S L W |
| SP1-46 | T K P P N P K P S M F F |
| SP1-13,47 | Q K P P N P S P I S P L |
| SP1-9,28,31,35,36,45 | K P P N P S P M S R F I |
| SP1-43 | K P P N P S P I E H W P |

TABLE 2-continued

Alignment of phage-displayed peptide sequences with complete genome of SARS-CoV[a]

| Virus or clone | | Peptide sequence | |
|---|---|---|---|
| SP1-53 | | K P P N P S P L A L A G | |
| SP1-58 | | K P P N P S H L S L T W | |
| SP1-54 | | K P P N P H P L P Y E S | |
| SP1-24 | | K P P N P P P P P H D L | |
| SP1-25 | | L K P P N P M P P A H G | |
| Virus | | | |
| SARS[1] | CDS4-17 | P V K I D N A S P A S T V | 29 |
| SARS[2] | CDS4-17 | P V K I D N A S P A S T V | 29 |
| SARS[3] | CDS4-17 | P V K I D N A S P A S T V | 29 |
| Clone | | | |
| SP1-8,19,26,49 | | V K I P N Y P P N S T S | |
| SP1-72 | | V K I P N S G T A L S R | |
| SP1-14 | | V K I Q N N P P P L P Q | |
| SP1-18 | | V K I P N T Y R L G M A | |
| SP1-38 | | V K I N N S S P L P T G | |
| SP1-39 | | V K I Q N L P T L N T K | |
| SP1-34,60 | | V K I P Q H I N L T S E | |
| SP1-12 | | V K I P Q F L A S P L A | |
| SP1-61 | | V K I S Q Y A S M P P I | |
| SP1-1 | | V K I P Q H M H P L P I | |
| SP1-16 | | V R I P N P P P T P F L | |
| SP1-42 | | V R I A N H P P E P F R | |

[a]The protein sequences of SARS-CoV retrieved from GenBank with the accession numbers of NC004718[1], AY278554[2] and AY278741[3], respectively.
[b]Phage-displayed consensus amino acids are shown in boldface.

TABLE 3

Alignment of phage-displayed peptide sequences selected by serum antibodies from SP2 SARS patient

| Clone | Peptide sequence |
|---|---|
| SP2-47 | T[a] N V F Y P P Q N S V D |
| SP2-25,45 | T N V L R P P A L S P S |
| SP2-4,10,16,23,33, 50,55,56,58,63 | N P F E Q F T Q S W R K |
| SP2-46 | N P F E S Y I N S G Y E |
| SP2-61,62 | N P L E L F T Q L Y S D |
| SP2-53 | N P L A Y F L A T Q V P |
| SP2-3 | N P M E E W V D F H S R |
| SP2-2 | L G W D R T Q M L P G D |
| SP2-27 | S Y H V W D P I I P L P |
| SP2-51,52 | Q I Y M W N P T A P L P |
| SP2-40 | H L E T W S P U T P L P |
| SP2-68 | G G P A Y F D L V R S V |

[a]Phage-displayed consensus amino acids are shown in boldface.

TABLE 4

Alignment of phage-displayed peptide sequences with
complete genome of SARS-CoV[a]

| Virus or clone | | Peptide sequence |
|---|---|---|
| Virus | | |
| SARS[1] | spike-582 | S V[b] I T P G T N A S [591] |
| SARS[2] | spike-582 | S V I T P G T N A S [591] |
| SARS[3] | spike-582 | S V I T P G T N A S [591] |
| Clone | | |
| SP3-29 | | V I T P Q P F K N T H R |
| SP3-71 | | G S Y Y I T P Q P P K P |
| Virus | | |
| SARS[1] | spike-790 | D P L K P T K R S F [799] |
| SARS[2] | spike-790 | D P L K P T K R S F [799] |
| SARS[3] | spike-790 | D P L K P T K R S F [799] |
| Clone | | |
| SP3-11 | | M P F Q Q P L K P G A I |
| SP3-7,9,53 | | H V P H P F M Q P L K P |
| SP3-44 | | F Y Q P L K P S P P S R |
| SP3-30 | | S Y I V A Q P L K P G T |
| SP3-48 | | A G H A S V K Q P L K |
| SP3-17 | | L L A R L P P Q P I K P |
| SP3-60 | | T E T P Q P I K P V S P |

[a]The protein sequences of SARS-CoV retrieved from GenBank with the accession numbers of NC004718[1], AY278554[2] and AY278741[3], respectively.
[b]Phage-displayed consensus amino acids are shown in boldface.

TABLE 5

Sensitivity and specificity for diagnosis of SARS patients

|  |  | SARS Test Result | | | |
|---|---|---|---|---|---|
|  |  | Positive | Negative | Sensitivity | Specificity |
| SARS Convalescent Serums (66) | | | | | |
| Phage clones | SP1-1 | 38 | 28 | 57.6% | |
|  | SP1-20 | 30 | 36 | 45.5% | |
|  | SP2-27 | 10 | 56 | 15.2% | |
|  | SP3-29 | 24 | 42 | 36.4% | |
| Peptide | SP3M | 40 | 26 | 60.6% | |
| Combination |  | 63 | 3 | 95.4% | |

TABLE 5-continued

Sensitivity and specificity for diagnosis of SARS patients

|  |  | SARS Test Result | | | |
|---|---|---|---|---|---|
|  |  | Positive | Negative | Sensitivity | Specificity |
| Healthy donors (22) | | | | | |
| Phage clones | SP1-1 | 1 | 21 |  | 95.4% |
|  | SP1-20 |  | 22 |  | 100% |
|  | SP2-27 |  | 22 |  | 100% |
|  | SP3-29 |  | 22 |  | 100% |
| Peptide | SP3M | 1 | 21 |  | 95.4% |

What is claimed is:

1. A SARS-CoV-specific B-cell epitope for diagnosing SARS patients, having at least one amino acid sequence selected from the group consisting of SEQ ID NO: 13, SEQ ID NO: 14 and SEQ ID NO: 15.

2. A SARS-CoV-specific B-cell epitope-based peptide for diagnosing SARS patients, having at least one amino acid sequence selected from the group consisting of SEQ ID NO: 13, SEQ ID NO: 14 and SEQ ID NO: 15.

3. The peptide according to claim 2, wherein the peptide is expressed in phage displayed clones.

4. The peptide according to claim 2, wherein the peptide is artificially synthesized.

5. An immunogen having at least one SARS-CoV-specific B-cell epitope for producing antibodies, wherein the epitope is selected from the group consisting of SEQ ID NO: 13, SEQ ID NO: 14 and SEQ ID NO: 15.

6. An immunogen having at least one SARS-CoV-specific B-cell epitope-based peptide for producing antibodies, wherein the peptide is selected from the group consisting of SEQ ID NO: 13, SEQ ID NO: 14 and SEQ ID NO: 15.

7. The immunogen according to claim 6, wherein the peptide is an artificially synthesized peptide.

* * * * *